(12) United States Patent
Gather et al.

(10) Patent No.: US 11,719,686 B2
(45) Date of Patent: Aug. 8, 2023

(54) MICRO-CAVITY-BASED FORCE SENSOR

(71) Applicant: University Court of the University of St Andrews, St Andrews (GB)

(72) Inventors: Malte C. Gather, Fife (GB); Nils Kronenberg, Fife (GB); Philipp Liehm, Fife (GB)

(73) Assignee: UNIVERSITY COURT OF THE UNIVERSITY OF ST. ANDREWS, St Andrews (GB)

( * ) Notice: Subject to any disclaimer, the term of this patent is extended or adjusted under 35 U.S.C. 154(b) by 665 days.

(21) Appl. No.: 15/531,118

(22) PCT Filed: Nov. 9, 2015

(86) PCT No.: PCT/GB2015/053395
§ 371 (c)(1),
(2) Date: May 26, 2017

(87) PCT Pub. No.: WO2016/083779
PCT Pub. Date: Jun. 2, 2016

(65) Prior Publication Data
US 2017/0322193 A1    Nov. 9, 2017

(30) Foreign Application Priority Data

Nov. 28, 2014  (GB) ..................... 1421214

(51) Int. Cl.
| | | |
|---|---|---|
| *G01N 33/483* | (2006.01) | |
| *G01N 13/00* | (2006.01) | |
| *G01L 5/00* | (2006.01) | |
| *G01L 1/24* | (2006.01) | |

(52) U.S. Cl.
CPC ............ *G01N 33/4833* (2013.01); *G01L 1/24* (2013.01); *G01L 5/0052* (2013.01); *G01N 13/00* (2013.01); *G01N 33/483* (2013.01); *G01N 2203/0089* (2013.01)

(58) Field of Classification Search
CPC .............................. G01N 33/4833; G01L 1/24
See application file for complete search history.

(56) References Cited

U.S. PATENT DOCUMENTS

| | | | |
|---|---|---|---|
| 4,405,197 | A | 9/1983 | Bejczy |
| 8,610,103 | B2 | 12/2013 | Menon et al. |
| 2004/0033482 | A1 | 2/2004 | Artmann |
| 2013/0133439 | A1 | 5/2013 | Axelrod |

(Continued)

FOREIGN PATENT DOCUMENTS

| | | |
|---|---|---|
| CN | 103 259 188 A | 8/2013 |
| GB | 2329243 | 3/1999 |
| WO | WO 2013/017814 A1 | 2/2013 |

OTHER PUBLICATIONS

Block, H, et al, Thermally tunable optical aperture based on a segmented thin-film resonator, (May 2, 2014), Proceedings of SPIE, vol. 9130, 7 pages (Year: 2014).*

(Continued)

*Primary Examiner* — Benjamin R Whatley
(74) *Attorney, Agent, or Firm* — Sheridan Ross P.C.

(57) ABSTRACT

A system for measuring cellular forces exerted on a surface comprising: a deformable sensor that has a deformable surface adapted to deform on application of a cellular force, and an optical detector for optically detecting deformation of the surface.

19 Claims, 10 Drawing Sheets

(56) References Cited

U.S. PATENT DOCUMENTS

| | | | | |
|---|---|---|---|---|
| 2014/0315213 A1* | 10/2014 | Nagrath | ............ | G01N 33/54353 435/7.1 |
| 2014/0318273 A1 | 10/2014 | Dong et al. | | |
| 2014/0336072 A1* | 11/2014 | Krishnan | ................ | B05D 3/007 506/9 |
| 2015/0184122 A1* | 7/2015 | Le Berre | .............. | C12N 5/0068 435/395 |
| 2017/0016875 A1* | 1/2017 | Parker | .................... | A61B 5/053 |

OTHER PUBLICATIONS

Block, H. et al, Thermally tunable optical aperture based on a segmented thin-film resonator, (May 2, 2014), Proceedings of SPIE, vol. 9130, 7 pages.*

Olympus IX70 Inverted MIcroscope; https://web.archive.org/web/20131010230330/https://micro.magnet.fsu.edu/primer/techniques/fluorescence/ix70fluorescence.html. Accessed on Apr. 12, 2022 and published online on Sep. 10, 2013; hereinafter "Olympus".*

International Search Report and Written Opinion prepared by the European Patent Office dated Feb. 23, 2016, for International Application No. PCT/GB2015/053395.

Jin-Yu Shao et al: "Micropipette suction for measuring piconewton forces of adhesion and tether formation from neutrophil membranes", Biophysical Journal Biophys. Soc. USA, vol. 71, No. 5, Nov. 1996 (Nov. 1996), pp. 2892-2901.

Jianping Fu et al: "Mechanical regulation of cell function with geometrically modulated elastomeric substrates", Nature Methods, vol. 7, No. 9, Sep. 1, 2010 (Sep. 1, 2010), pp. 733-736.

Yang Shengyuan et al: "Micromachined force sensors for the study of cell mechanics", Review of Scientific Instruments, AIP, Melville, NY, US, vol. 76, No. 4, Mar. 16, 2005 (Mar. 16, 2005), pp. 44301-044301.

Block et al. "Thermally tunable optical aperture based on a segmented thin-film resonator," Visual Communications and Image Processing, vol. 9130, 913002, May 2014, 7 pages.

Campas et al., "Quantifying cell-generated mechanical forces within living embryonic tissues," Nature Methods, vol. 11, No. 2, Feb. 2014, pp. 183-189.

Delanoe-Ayari et al., "4D Traction Force Microscopy Reveals Asymmetric Cortical Forces in Migrating Dictyostelium Cells," Physical Review Letters, vol. 105, No. 248103, Dec. 10, 2010, 5 pages.

Grashoff et al., "Measuring mechanical tension across vinculin reveals regulation of focal adhesion dynamics," Nature, vol. 466, No. 7303, Jul. 8, 2010, pp. 263-266.

Hall et al., "Towards Single Cell Traction Microscopy within 3D Collagen Matrices," Experimental Cell Research, vol. 319, No. 16, Oct. 1, 2013, pp. 2396-2408.

Hur et al., "Live Cells Exert 3-Dimensional Traction Forces on Their Substrata," Cellular and Molecular Bioengineering, vol. 2, No. 3, Sep. 2009, pp. 425-436.

Klein et al., "Elastic Fully Three-dimensional Microstructure Scaffolds for Cell Force Measurements," Advanced Materials, vol. 22, 2010, pp. 868-871.

Legant et al., "Multidimensional traction force microscopy reveals out-of-piane rotational moments about focal adhesions," PNAS, vol. 110, No. 3, Jan. 15, 2013, pp. 881-886.

Maskarinec et al., "Quantifying cellular traction forces in three dimensions," PNAS, vol. 106, No. 52, Dec. 29, 2009, pp. 22108-22113.

Search Report for United Kingdom Patent Application No. GB1421214.6, dated Apr. 16, 2015, 3 pages.

* cited by examiner

MICRO-CAVITY-BASED FORCE SENSOR

CROSS REFERENCE TO RELATED APPLICATIONS

This application is a national stage application under 35 U.S.C. 371 and claims the benefit of PCT Application No. PCT/GB2015/053395 having an international filing date of 9 Nov. 2015, which designated the United States, which PCT application claimed the benefit of Great Britain Application No. 1421214.6 filed 28 Nov. 2014, the entire disclosures of each of which are incorporated herein by reference.

INTRODUCTION

The present invention relates to a micro-cavity based force sensor for sensing the force applied by cells.

BACKGROUND OF THE INVENTION

Biological cells can apply forces to their surrounding environment and sense the mechanical forces of their environment. The surrounding environment may be made up of the extracellular matrix and neighbouring cells. The force a live cell applies to its surrounding environment may influence cellular functions, for example cell migration, division, growth, communication, metabolism, and programmed cell death.

When doing research on cellular forces the cytoskeleton is important. The cytoskeleton in cells is a dynamic construct of proteins, assembling and disassembling to support the functions of the cell. This dynamic nature allows a fast response to external and internal stimuli which is vital for the function and survival of the cell. Structural support when encountering external stress is one of the main functions of the cytoskeleton. However, it is also crucial for fast directional transport of organelles and chemicals inside the cell as well. Cell movement is usually based on polymerisation of parts of the cytoskeleton at the leading edge, e.g. actin, and depolymerisation at the other end of the cell.

The cytoskeleton is comprised of three main components: microtubules, intermediate filaments, and actin. All three are based on monomers which bind together to more complex polymer structures.

Microtubules form strong pillars reaching from the cell nucleus to the edge of the cell. They form polarised polymers allowing bidirectional cargo transport inside the cell by molecular motors like dynein and kinesin.

Actin forms tightly wound helical filaments which are less rigid than microtubules. However, they can bind to cross-linking proteins to form different types of highly organised, stiff structures. The continuous polymerisation of actin at the leading edge of the cell is a key player in sensing the environment and cell movement.

Intermediate filaments are simply called "intermediate" because their diameter of around 10 nm is between the diameter of microtubules (25 nm) and actin filaments (7 nm). They are less stiff than microtubule and actin filaments and are not polarised like the other two polymers. Hence, they are not suitable for transport via molecular motors. Due to their high flexibility and resistances against tensile forces, intermediate filaments highly support the integrity of the whole tissue and the cell itself. A subgroup of the intermediate filaments is the keratin filaments, which are mainly found in epithelial cells. They establish cell-cell contact and combine those junctions with filaments inside the cell itself. Tensile forces which occur during stretching, for example of skin, can therefore be compensated by the array of cells. A failure in keratin production (e.g. due to a genetic defect) can lead to serious diseases like epidermolysis bullosa simplex where the human skin is highly vulnerable to mechanical stress.

Focal adhesions are large macromolecular assemblies, which bind to the extracellular matrix. Besides anchoring the cell to the extracellular matrix, they also serve as signalling interface between the extracellular matrix and the cell. The cell—extracellular matrix connection generally involves integrins. The focal adhesion—cytoskeleton contact is established by adapter proteins, e.g. vinculin. However, there are more than one hundred different proteins involved in focal adhesion formation indicating a high functional diversity.

Figure 1:
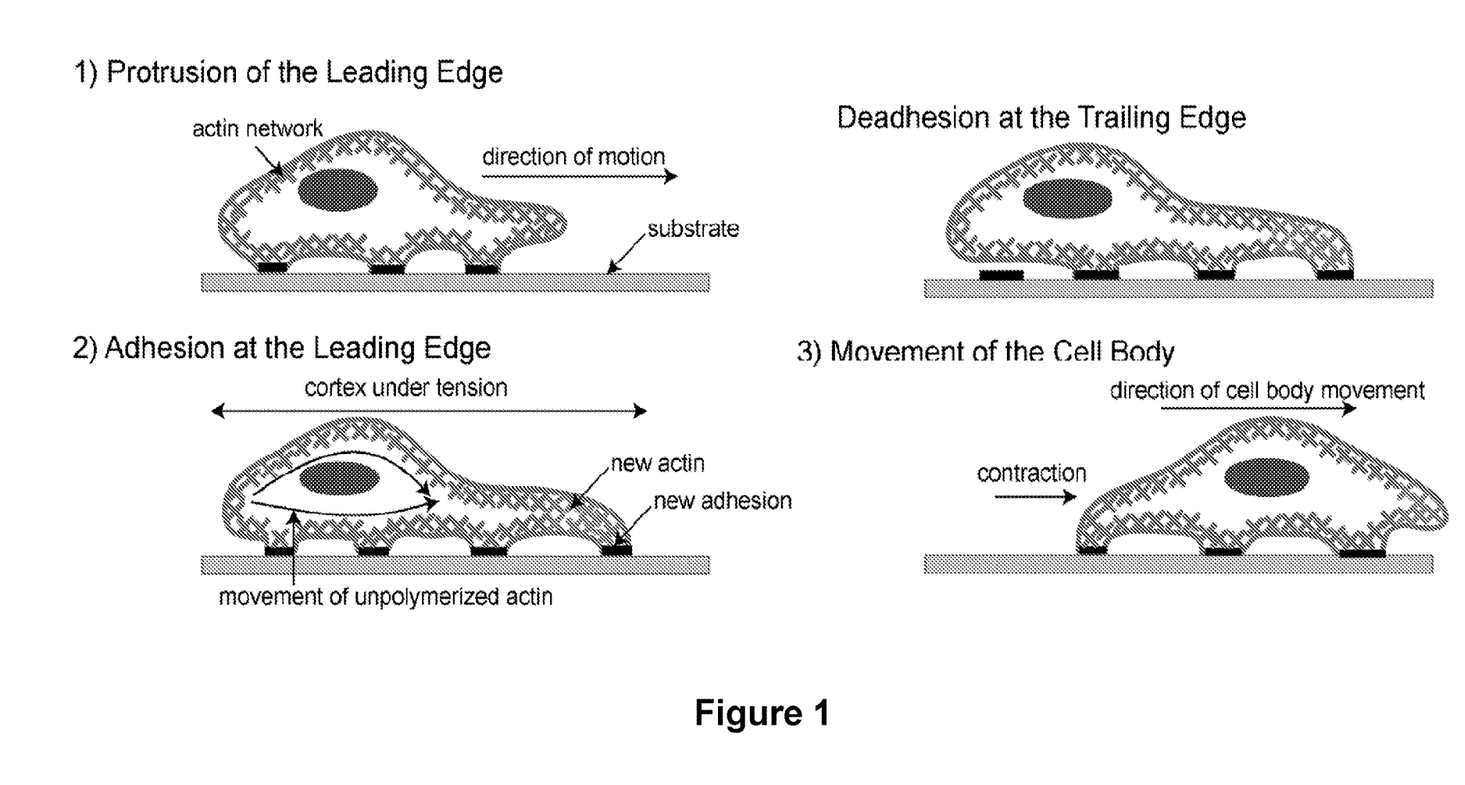
FIG. 1 is a schematic view of a cell moving along a surface.

FIG. 1 shows a simplified schematic illustrating cell movement. If a cell senses external stimuli like chemical cues or a change in the physical environment, this can lead to a formation of protrusions like lamellipodia. This is driven by actin monomers assembling at the leading edge of the cell (in the direction of motion) polymerising into actin filaments and networks, as shown in FIG. 1(1). Then a new focal adhesion is formed to anchor the cell at the front, as shown in FIG. 1(2). The whole cell is then pulled forwards by actin myosin interactions similar to the contraction happening in muscle cells, and the trailing edge is lifted from the substrate, as shown in FIG. 1(3). At the back of the cell the actin network and the focal adhesion is depolymerised to allow further movement, as shown in FIG. 1(4). Throughout the process forces are applied to the substrate. Measuring these forces can contribute to a comprehensive understanding of this process.

Different methods have been developed to measure the forces exerted by a cell. In general, these methods involve monitoring the response of the surrounding environment to the force exerted by the cell. This allows the force to be measured indirectly. A known method of measuring cell force is Traction Force Microscopy (TFM). Cells make contact with their environment through focal adhesions. Traction stresses between the adhesions and the extracellular matrix drives cell division, migration in morphogenesis, wound healing and tumour metastasis. TFM involves cultivating cells on a substrate comprising a soft hydrogel. Soft fluorescent beads are embedded inside the hydrogel. In response to cellular traction forces the beads inside the hydrogel are displaced. The displacements of all the beads in the hydrogel are tracked using a confocal microscope. The forces at every bead can then be calculated.

Conventional TFM, and other methods of measuring cellular forces, are based on the assumption that cells exert horizontal tractions only in the plane of the accommodating substrate. However, it has been shown by Hur et al. "Live Cells Exert 3-Dimensional Traction Forces on Their Substrata", Cell. Mol. Bioeng. 2, pp. 425-436 (2009), that cells also exert forces normal to this plane in a vertical direction. The magnitude of the vertical force exerted is comparable to the magnitude of the horizontal force. To address this problem, TFM was further developed in Hur et al. to a method known as 2.5D TFM. In this, additional fluorescent beads are embedded deeper in the gel, as opposed to simply lying on the surface. The focus of the confocal microscope is then varied in the vertical direction to measure the perpendicular displacement of the beads. A problem with 2.5D TFM is that the need to also scan in vertical direction can make the method slow. Also large amounts of data need to be analysed to track the position of the fluorescent beads.

There is also a danger of damaging the cell by the prolonged exposure of the laser probe beam that is required for 2.5D TFM.

SUMMARY OF THE INVENTION

According to the present invention, there is provided a cell force sensor based on an elastic micro-cavity. The sensor has an upper surface that is resiliently deformable in response to the presence of one or more live cells on its surface or movement of such cells on the surface. When an adhered cell on top of the sensor pushes and/or pulls, e.g. through its focal adhesions, it exerts forces onto the sensor. This causes changes in the local thickness of the micro-cavity. Such local thickness changes can be detected optically.

For example, the thickness changes can be detected using a microscope and a variable wavelength illumination lightsource. An interference pattern can be observed that is dependent on the local sensor thickness and the applied wavelength. By taking images across a range of wavelengths, the reflectivity spectrum for every pixel within an image can be measured. This allows the thickness of the cavity to be measured at every pixel. This thickness information can then be converted into spatially resolved information on the force applied by the cell to the surface.

According to one aspect of the invention, there is provided a system for measuring cellular forces exerted on a surface comprising: a deformable sensor that has a deformable surface adapted to deform on application of a cellular force, and an optical detector for detecting deformation of the surface using light.

The detector may be operable to detect a thickness change and determine cellular forces using the detected thickness change.

The deformable sensor may have an optical cavity that has a thickness that is a function of the cellular force applied to the deformable surface The deformable sensor may comprise at least two layers of reflective material for defining the optical cavity. One of the layers of reflective material may define the optical cavity.

A layer of elastic/deformable/compressible material may be provided between the reflective layers. The reflective material may comprise metal. The elastic/deformable/compressible material may comprise an elastomer.

According to another aspect of the invention, there is provided a deformable sensor for measuring cell force comprising a resiliently deformable surface adapted to deform on application of a cellular force and an optical cavity that has a thickness that is a function of the cellular force applied to the deformable surface.

The deformable sensor may comprise at least two layers of at least partially reflective material for defining the optical cavity. A layer of elastic/deformable/compressible material may be provided between the reflective layers. The reflective material may comprise metal. The elastic/deformable/compressible material may comprise an elastomer.

The deformable surface may be on top of the elastic/deformable/compressible material, and the elastic/deformable/compressible material may have a thickness that is a function of cellular force applied to the deformable surface.

The deformable surface may be adapted to deform on application of a pushing and/or pulling force applied by the cell.

According to another aspect of the invention, there is provided a method for measuring cellular forces using a deformable sensor that has a deformable surface adapted to deform on application of a cellular force, and an optical cavity that has a thickness that is a function of the cellular force applied to the deformable surface, the method involving: transmitting light into the optical cavity when a cell is on the deformable surface; detecting light emitted from the optical cavity, and using the detected light to determine the cellular force.

The method may involve varying the wavelength of the light transmitted into the optical cavity and detecting the light emitted from the cavity as a function of wavelength. The method may further involve using the detected light to identify at least one resonant wavelength and using the at least one resonant wavelength to determine the cellular force.

The detector may have multiple pixels, each associated with an area of the deformable surface. In this case, light is detected at each pixel, so that cellular force is determined at different areas of the deformable surface.

The cellular force measured may be cellular adhesion. To measure this, the method may further involve removing a cell from the deformable surface, and determining the force at which the cell is removed. A fluid flow may be is used to remove the cell from the deformable surface. A mechanical device may be used to pull the cell from the deformable surface. A suction device may be used to pull the cell from the deformable surface.

According to yet another aspect of the invention, there is provided a method of fabricating a deformable sensor comprising: depositing a first semitransparent reflective layer, for example a metal such as gold, on a substrate; forming a layer of elastic/deformable/compressible material on the first semitransparent reflective layer, and depositing a second semitransparent reflective layer, for example gold on the layer of elastic/deformable/compressible material.

The method may further involve depositing an adhesion layer on the substrate prior to deposition of the first semitransparent reflective layer. The adhesion layer may comprise chromium.

The method may further involve forming or depositing a transparent adhesion layer, for example a layer of $SiO_2$, on the first semitransparent reflective layer prior to deposition of the elastic/deformable/compressible material.

The method may further involve oxidising the elastic/deformable/compressible material prior to deposition of the second semitransparent reflective layer.

According to still another aspect of the invention, there is provided a method for measuring cellular forces exerted on a surface using a deformable sensor that has a deformable surface adapted to deform on application of a cellular force, and an optical cavity that has a thickness that is a function of the cellular force applied to the deformable surface, the method involving: transmitting light into the optical cavity when a cell is on the deformable surface; detecting light emitted from the optical cavity, and using the detected light to determine the cellular force.

The method may involve varying the wavelength of the light transmitted into the optical cavity and detecting the light emitted from the cavity as a function of wavelength. The method may involve using the detected light to identify at least one resonant wavelength and using the at least one resonant wavelength to determine the cellular force.

The detector may have multiple pixels, each associated with an area of the deformable surface, and light is detected at each pixel, so that cellular force is determined at different areas of the deformable surface.

The cellular force measured may be cellular adhesion force. This may be measure by removing a cell from the deformable surface, wherein the force at which the cell is removed from the surface represents the cellular adhesion. A fluid flow may be used to remove the cell from the deformable surface. A mechanical device may be used to pull the cell from the deformable surface. A suction device may be used to pull the cell from the deformable surface.

According to still another aspect of the invention, there is provided a system for measuring cellular forces exerted on a surface, the system being adapted to: transmit light into an optical cavity when a cell is on a deformable surface associated with the cavity; detect light emitted from the optical cavity, and use the detected light to determine the cellular force.

The system may be adapted to vary the wavelength of the light transmitted into the optical cavity and detect the light emitted from the cavity as a function of wavelength.

The system may be adapted to use the detected light to identify at least one resonant wavelength and using the at least one resonant wavelength to determine the cellular force.

The system may include a detector that has multiple pixels, each associated with an area of the deformable surface. The detector may be adapted to detect light at each pixel, and the system may be adapted to use that detected light to determine cellular force at different areas of the deformable surface.

The cellular force measured may be cellular adhesion force. This may be measured by removing a cell from the deformable surface, wherein the force at which the cell is removed from the surface represents the cellular adhesion.

The system may be adapted to remove a cell from the surface. For example, a fluid flow may be used to remove the cell from the deformable surface. A mechanical device may be used to pull the cell from the deformable surface. A suction device may be used to pull the cell from the deformable surface.

BRIEF DESCRIPTION OF THE DRAWINGS

Various aspects of the invention will now be described by way of example only and with reference to the accompanying drawings, of which.

DETAILED DESCRIPTION OF THE DRAWINGS

Figure 2:
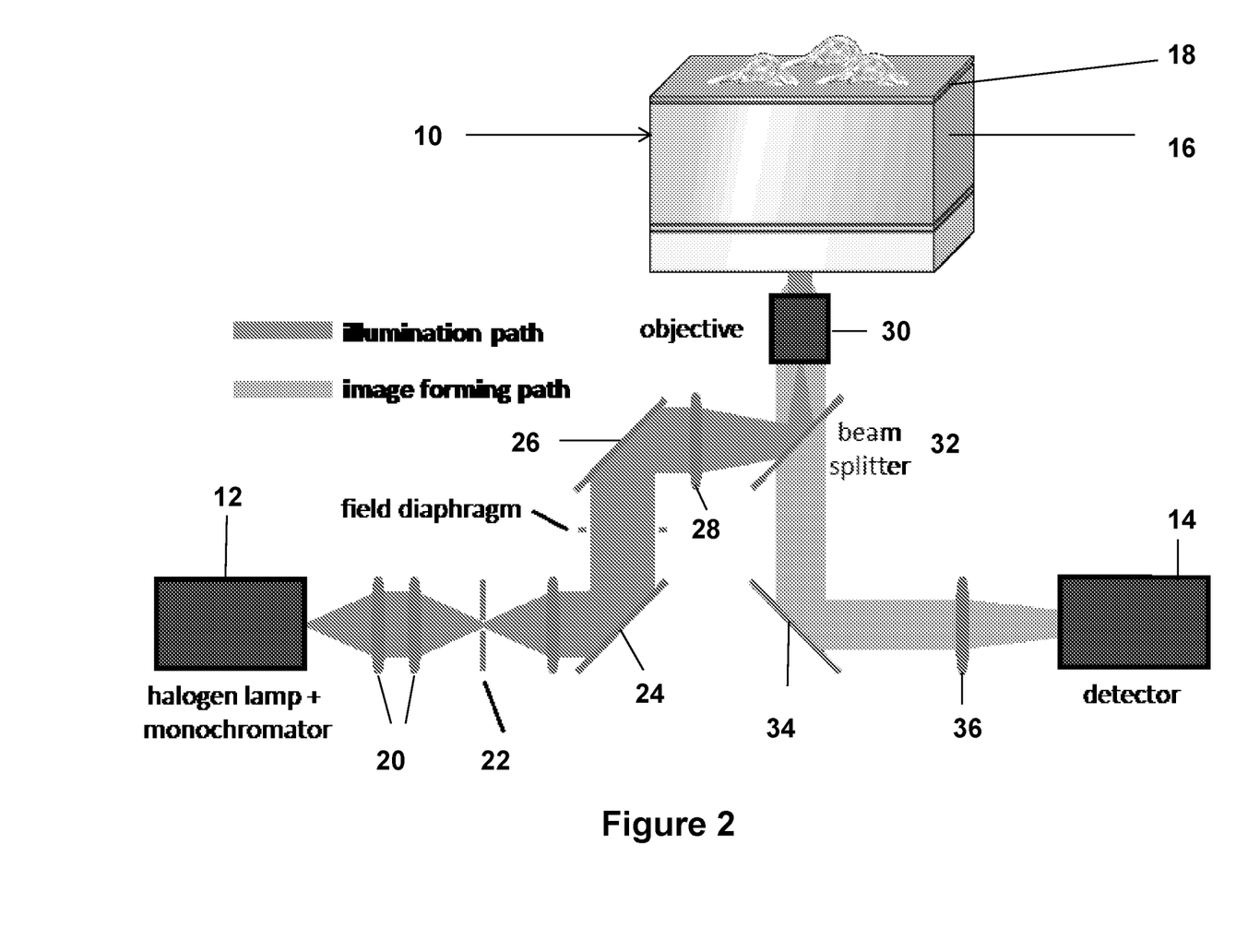
FIG. 2 is a schematic view of a cell force detection system.

FIG. 2 shows a cell force detection system. This has a micro-cavity sensor 10, a variable wavelength light source 12 and a detector 14. Between the light source 12 and the detector 14 are optical components for conditioning and guiding light from the source to the sensor 10, and directing light from the sensor to the detector 14. The micro-cavity sensor 10 has a main body 16 that is semitransparent to light from the source and an upper, reflective sample surface 18 on the main body 16 that is resiliently deformable in response to a cell, and in particular cell movement, on its surface. Deformation of the sample surface 18 causes changes in the thickness of the main body 16 of the sensor 10.

Light is directed from the source 12 to an underside of the micro-cavity sensor 10, so that it can pass through the main sensor body 16 to a backside of the upper reflective sample surface 18. Light reflected from the sample surface 18 is directed to the detector 14. An interference pattern can be observed that is dependent on the local sensor thickness and the applied wavelength. By taking images across a range of wavelengths, the reflectivity as a function of wavelength for every pixel within an image can be measured. This allows the thickness of the cavity to be measured. This in turn provides a measure of the force applied by the cell to the surface.

The excitation path and the detection path of the cell force system of FIG. 2 will now be described in more detail.

On the excitation path is the source 12, for example a halogen lamp (which has a relatively broadband output) and a monochromator for allowing selection of a single wavelength output. Light from the source 12 is collimated using a pair of lenses 20 and then focused towards an aperture diaphragm 22. Light that passes through the aperture diaphragm 22 is collimated and directed onto a mirror 24, which directs the collimated light towards another mirror 26. The collimated light is then passed to a lens 28, which focuses it onto an objective lens 30, which directs a highly collimated beam onto the backside of the upper reflective sample surface 18.

Between the lens and the objective 30 is a beam splitter 32 that allows light reflected from the reflective upper surface 18 to pass along the detection path towards a mirror 34, which then reflects the light onto a lens 36 that subsequently focuses the light onto the detector 14. The detector 14 has multiple pixels, each of which is mapped to a specific area on the sensor associated with the excitation beam. In one example, the detector 14 has 1280 by 1280 pixels and the corresponding total sample probe area is 300 microns by 300 microns.

In use, the source 12 (i.e. lamp and monochromator combination) is used to provide a variable wavelength output. To detect the thickness of the micro-cavity and consequently estimate the force applied by a cell, measurements are taken for a plurality of discrete, monochromatic wavelengths. For every wavelength, light is detected at each detector pixel. Hence, for every wavelength a measure of the micro-cavity thickness across the sample area can be determined. By repeating the measurement for multiple wavelengths a map of light reflected as a function of wavelength can be built up for every detector pixel and its corresponding sample area.

Figure 3:
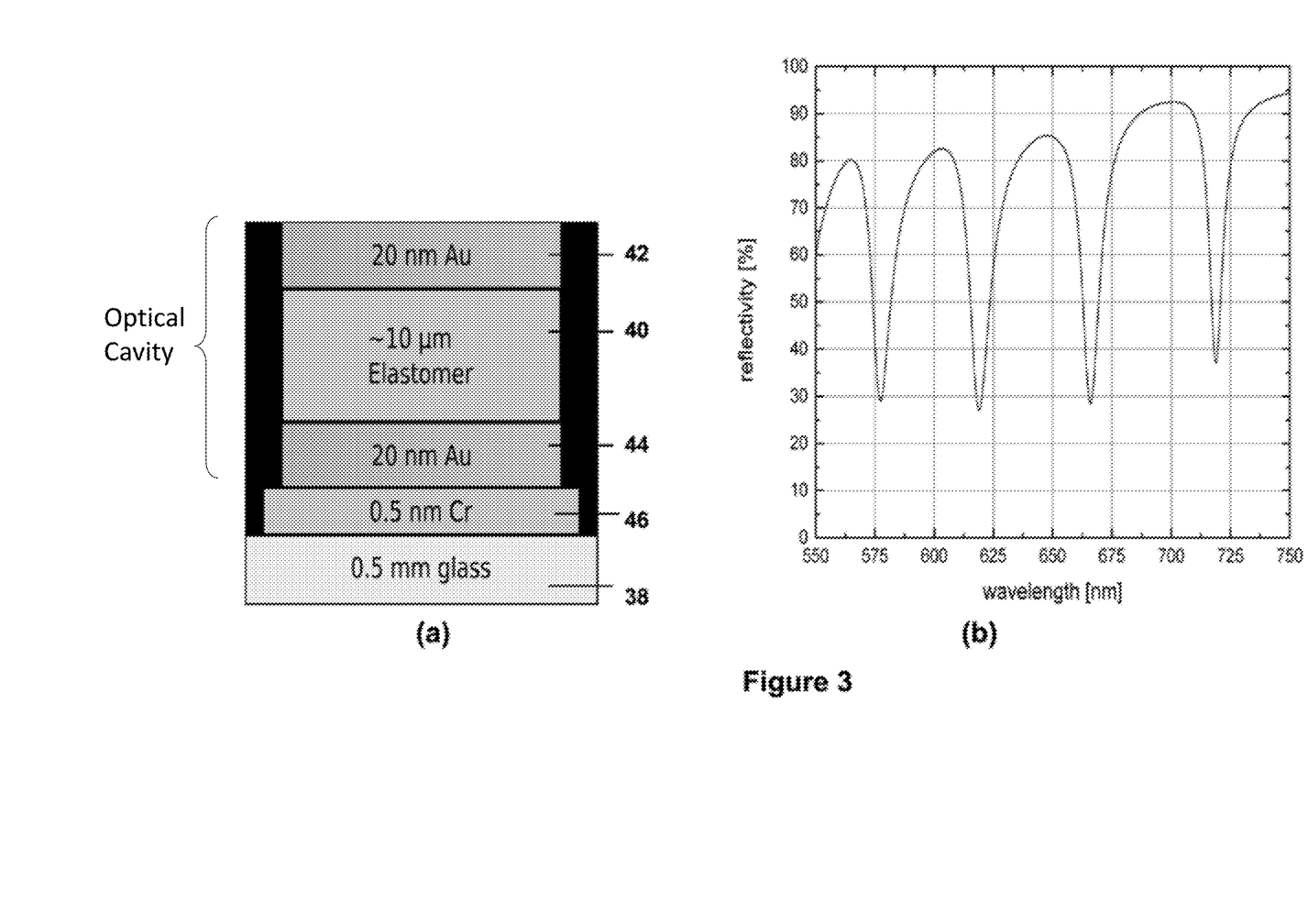
FIG. 3(a) is a detailed view of a cell force sensor of the detection system of FIG. 2.
FIG. 3(b) is a plot of reflectivity versus wavelength for the cell force sensor of FIG. 3(a)

FIG. 3 is a schematic view of a specific embodiment of the micro-cavity sensor 10. The sensor has a layered structure. The base layer is a glass layer 38. Above this, an elastic layer 40 is between an upper mirror layer 42 and a lower mirror layer 44. Together, the upper and lower mirror layers 42 and 44 and the elastic layer 40 form a micro-cavity. An adhesive layer 46 is between the micro-cavity and the glass layer 38. The upper and lower mirror layers 42 and 44 and the elastic layer 40 are semi-transparent. The lower mirror layer 44 allows a substantial amount of light to pass into the micro-cavity, so that the light can be transmitted into the micro-cavity.

As an example, the upper and lower mirror layers 42 and 44 are 20 nm thick layers of gold. The thickness of both the upper and lower mirror 42 and 44 were varied and optimized to find a trade-off between the contrast of interference, the light transmission through the sensor and the bending stiffness of the sensor. The elastic layer is manufactured from a polysiloxane-based elastomer and has a thickness of approximately 10 μm and a Young's modulus of 0.5 kPa. The adhesion layer enhances the adhesion of the lower mirror layer to the glass layer. As an example, the adhesion layer comprises a 0.5 nm layer of chromium.

In use, monochromatic light is incident on the sensor 10. Light enters the sensor by passing through the glass layer 38 and the lower semi-transparent mirror layer 44. The two mirror layers 42 and 44 act on the incident light to form an interference pattern in the cavity. The interference pattern is dependent on the local cavity thickness and the wavelength of the incident light. For a given local cavity thickness the incident light from the probe beam may be substantially absorbed. This occurs when the wavelength of the incident light fulfils the resonant conditions for the local cavity thickness. Substantially absorbed light will result in a minimum in a reflectance measurement. The sensor of FIG. 3 was fabricated as follows. A polysiloxane-based elastomer with a Young's modulus of 0.5 kPa was sandwiched between two semitransparent gold mirrors. This involved evaporation on the glass substrate of a 0.5 nm thick layer of chromium. This is used for adhesion purposes. On top of this, a 10 nm thick layer of gold and a 50 nm thick layer of $SiO_2$ were deposited using e-beam evaporation. The layer of $SiO_2$ improves adhesion with the elastomer. The two components of the elastomer were thoroughly mixed in a 1:1 ratio by volume, degassed under vacuum, spin coated onto the substrate and cross linked on a hot plate at 100 C for an hour.

Next, the surface of the elastomer layer was oxidised in a plasma asher and 15 nm of Au was thermally evaporated onto the elastomer to complete the optical cavity. The thicknesses of the top and bottom mirror were optimised to trade-off the contrast of the interference, the light transmission through the sensor and the bending stiffness of the sensor. The Young's modulus of the complete sensor was quantified as 20 kPa using atomic force microscope indentation measurements. To provide binding sites for cell adherence, a 14 nm thick layer of collagen type-1 was spin coated on top of the upper sample surface of the micro-cavity. A silicon chamber well (not shown) was adhered to the sensor surface to restrict the area of the sensor in contact with the cell medium. Prior to seeding of cells, the interior of the well was disinfected with an ethanol solution.

Cellular forces exerted on the surface of the sensor were measured by detecting the thickness change of the cavity and applying finite element analysis to convert the displacement fields into force information. The local thickness of the sensor was determined by a spatially resolved measurement of the resonant wavelength of the cavity over an area of 250 μm by 250 μm with megapixel resolution. For this purpose, the reflectance of the sensor was measured using monochromatic light (with a full width half maximum of 5-6 nm) in the wavelength range between 550 nm and 750 nm in 1 nm steps. The probe light was provided by a halogen lamp and a monochromator with a 1200 $nm^{-1}$ grating (grazing wavelength: 650 nm) and slits of 0.6 mm widths. The probe light was focused onto the rear focal plane of an objective lens (×40) of an inverted fluorescence microscope. The probe beam entered the sensor through the glass substrate and the bottom mirror and caused the formation of an interference pattern between the two mirrors. The resonant wavelengths for each pixel depended on both the local thickness of the elastomer cavity and the wavelength of the probe beam. Minima in the reflectance were detected for wavelengths fulfilling the resonant conditions for the local cavity thickness. The reflected interference pattern was imaged through the same objective lens used for illumination and recorded by means of a CMOS detector.

In order to ensure that the cells did not sense the hard glass substrate underneath the soft cavity, the cavities were produced with elastomer thicknesses in the range of 8-9 μm. This resulted in the appearance of multiple resonant wavelengths in the scan range. Two successive resonant peaks were separated by a free spectral range of 10-20 nm. To extract the local thickness of the cavity from the reflectance scans with an accuracy of less than 5 nm at least 10 resonant minima had to be measured. This imposed the use of a scan range of around 200 nm. The time required for one wavelength scan and thus the time resolution for the measurement technique was below 10 seconds, mainly limited by the communication between the analytical software and the monochromator, the frame rate of the camera, and the intensity of the monochromatic probe light.

The semitransparent optical properties of the cavity sensor (average transmission of about 12% in the wavelength measurement range) enabled the simultaneous recording of transmission based microscopy images (brightfield and phase contrast) as well as the alternating recording of fluorescence images via a second camera port using the standard imaging modes of the microscope.

To determine the local cavity thickness in experiments, a graph of reflectance against wavelength was stored. An example of this is shown in FIG. 3(b). The reflectance minima (which correspond to the resonant wavelengths) were localised using a fast minima localising algorithm and the set of resonant wavelengths for each pixel was compared to sets of previously computed resonant wavelengths of the cavity with identical setup using the natural, undeformed thickness of the elastomer as a reference and applying a transfer matrix algorithm.

Figure 4:
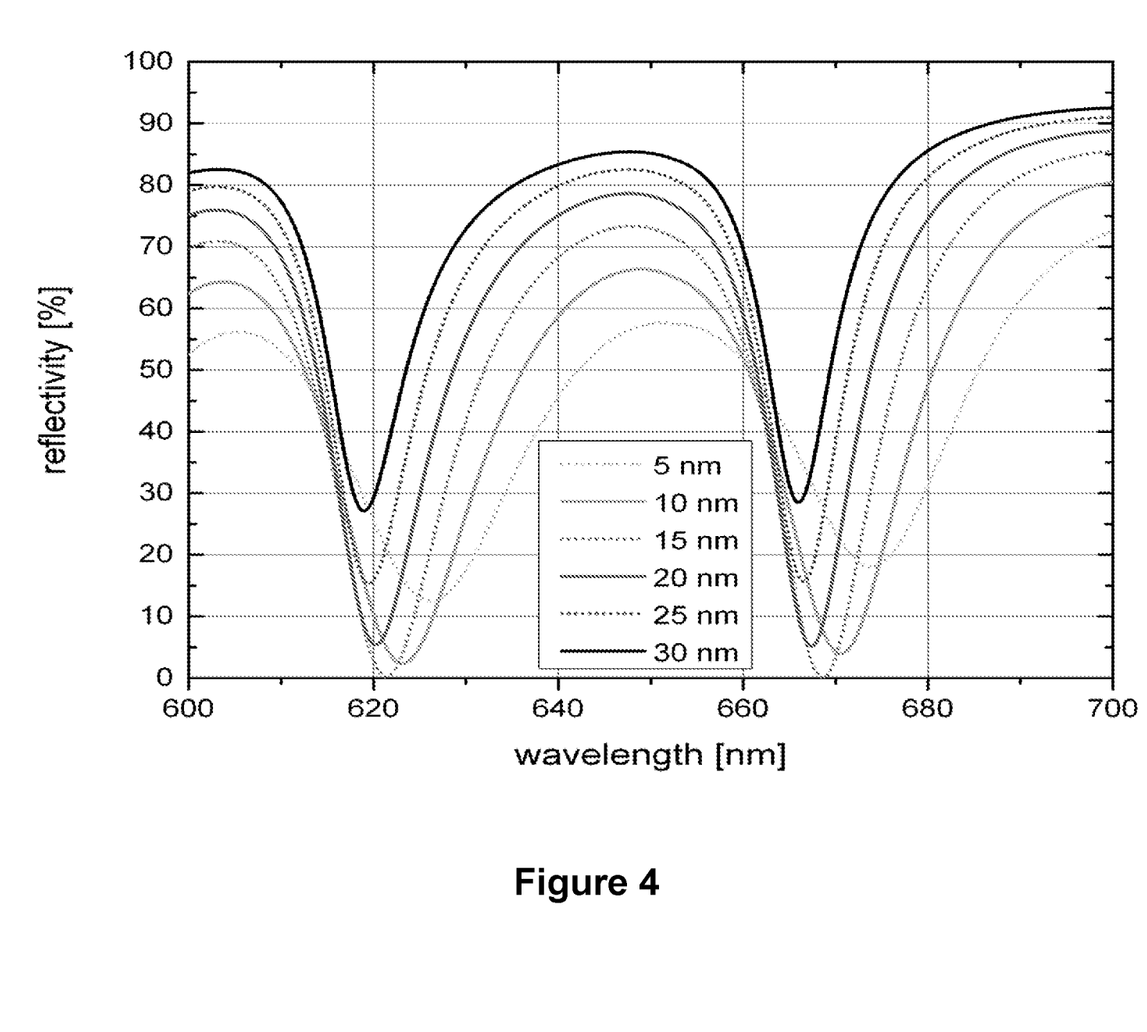
FIG. 4 is a plot of reflectivity versus wavelength for various cell force sensors lower layers of different thickness (5-30 nm)

To optimise the performance of the sensor various parameters had to be considered. In particular since the light used for the read-out comes from below (through the substrate), the bottom mirror needs allow a substantial amount of light to pass in order to observe interference. To find the optimal thickness for the bottom mirror, a variation of from 5 nm to 30 nm was simulated. The results of this are shown in FIG. 4. In this variation, the top mirror and the elastomer thickness were kept constant with 20 nm and 3000 nm respectively. Simulations showed that a bottom gold mirror of 20 nm shows the highest difference between minima and maxima. Thicker gold layers (e.g. 30 nm) increase the height of the maxima but also increase the height of the minima. Thinner gold layers show only slightly lower minima but much lower maxima.

Figure 5:
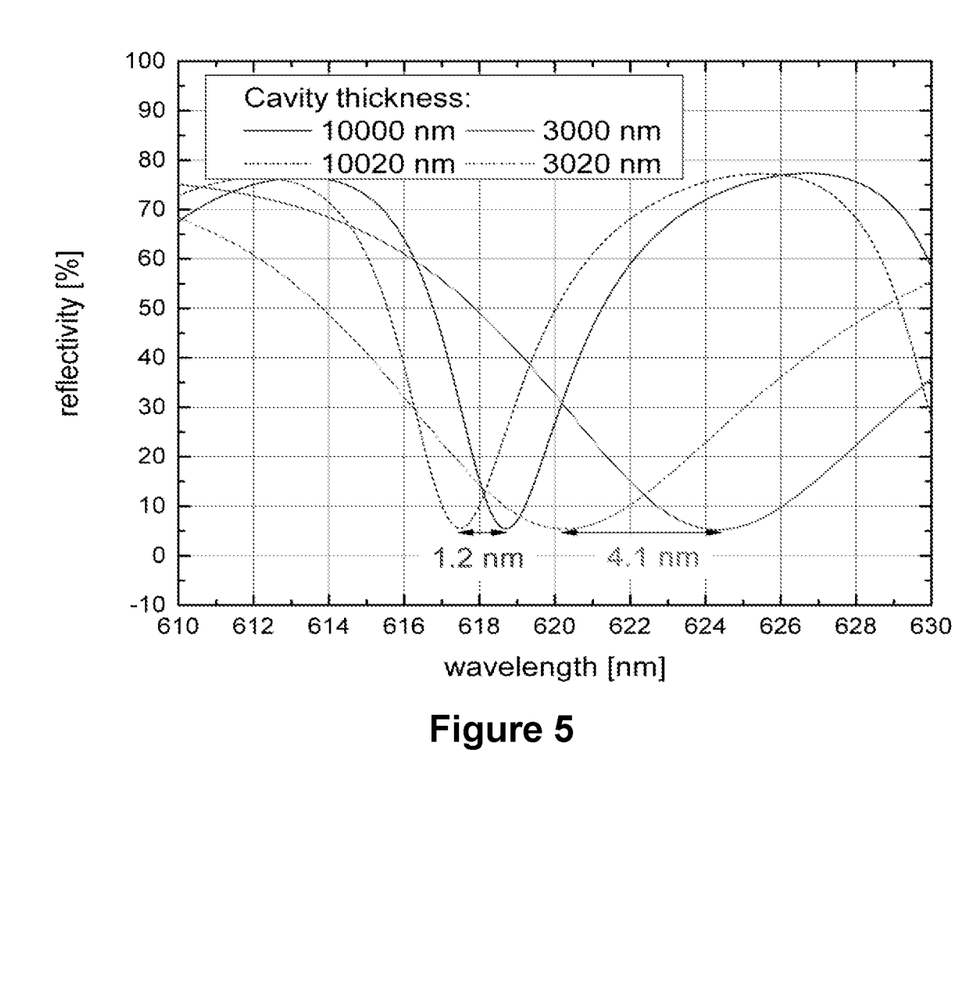
FIG. 5 is a plot of reflectivity versus wavelength for two different cell force sensors, each for two different thicknesses.

As well as the lower mirror, the thickness of the elastomer had to be chosen. In the literature, it has been shown that cells can feel a stiff substrate below a soft material if the thickness of the soft material is too small. However, optical simulations show that for a displacement of e.g. 20 nm the shift of the reflection minima is larger for smaller cavities than for thicker ones. This is shown in FIG. 5. The reflection minima distance for a 3000 nm and 3020 nm thick cavity is calculated as 4.1 nm whereas for 10000 nm and 10020 nm it is only 1.2 nm. Hence, in terms of sensitivity to cavity thickness changes, a thinner cavity is preferred.

Figure 6:
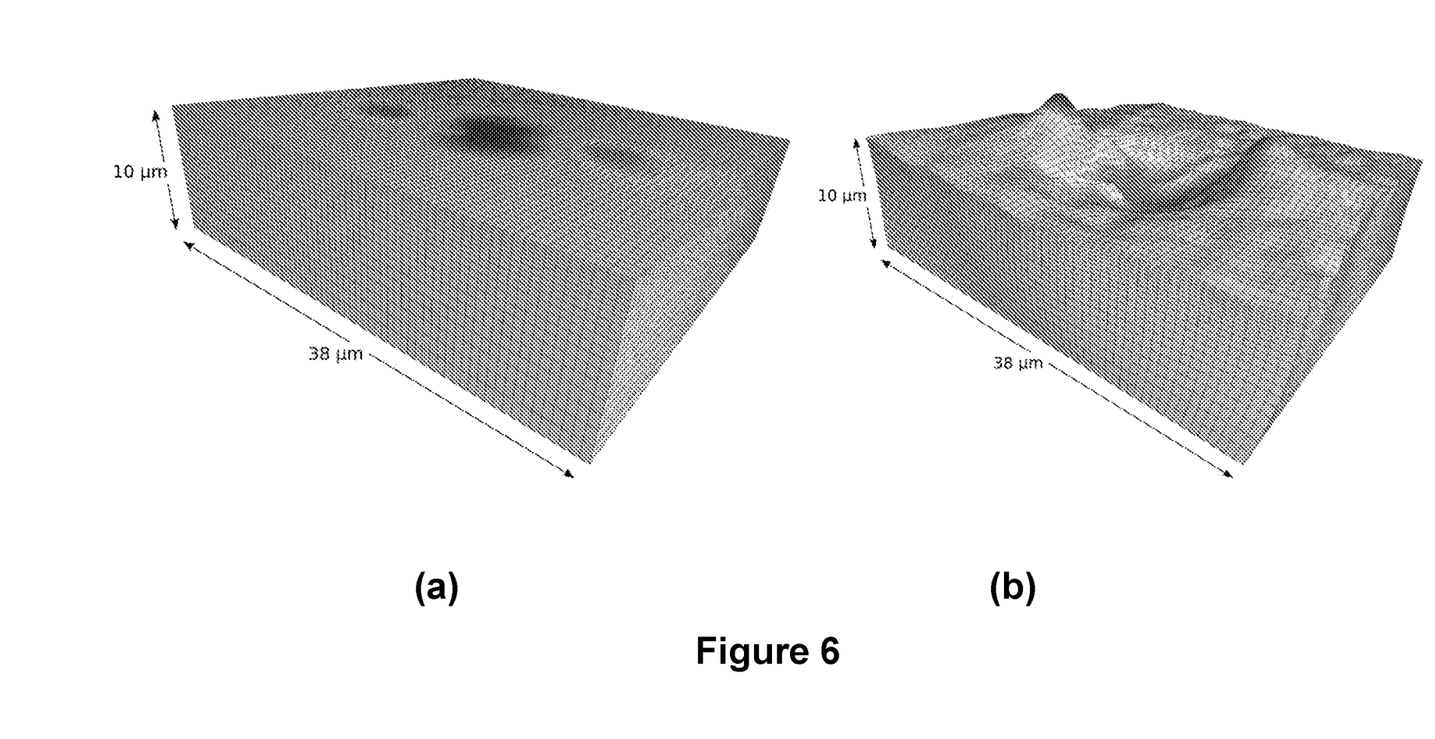
FIG. 6(a) is a 3D displacement map generated by finite element calculations, in which the different colours represent displacement.
FIG. 6(b) is a 3D force map generated using the displacement data of FIG. 6(a), in which the different colours represent different forces—here to make small displacements visible the force is enhanced by a factor of 100.

FIG. 6 shows a 3D displacement map generated by comparing the measured resonant wavelengths against optical simulations, in which the different colours represent displacement. FIG. 6(b) is a 3D force map generated by applying finite element calculations to the displacement data of FIG. 6(a), in which the different colours represent different forces. To make the small displacements in z-direction that cause the forces visible, the displacements are enhanced by a factor of 100.

Figure 7:
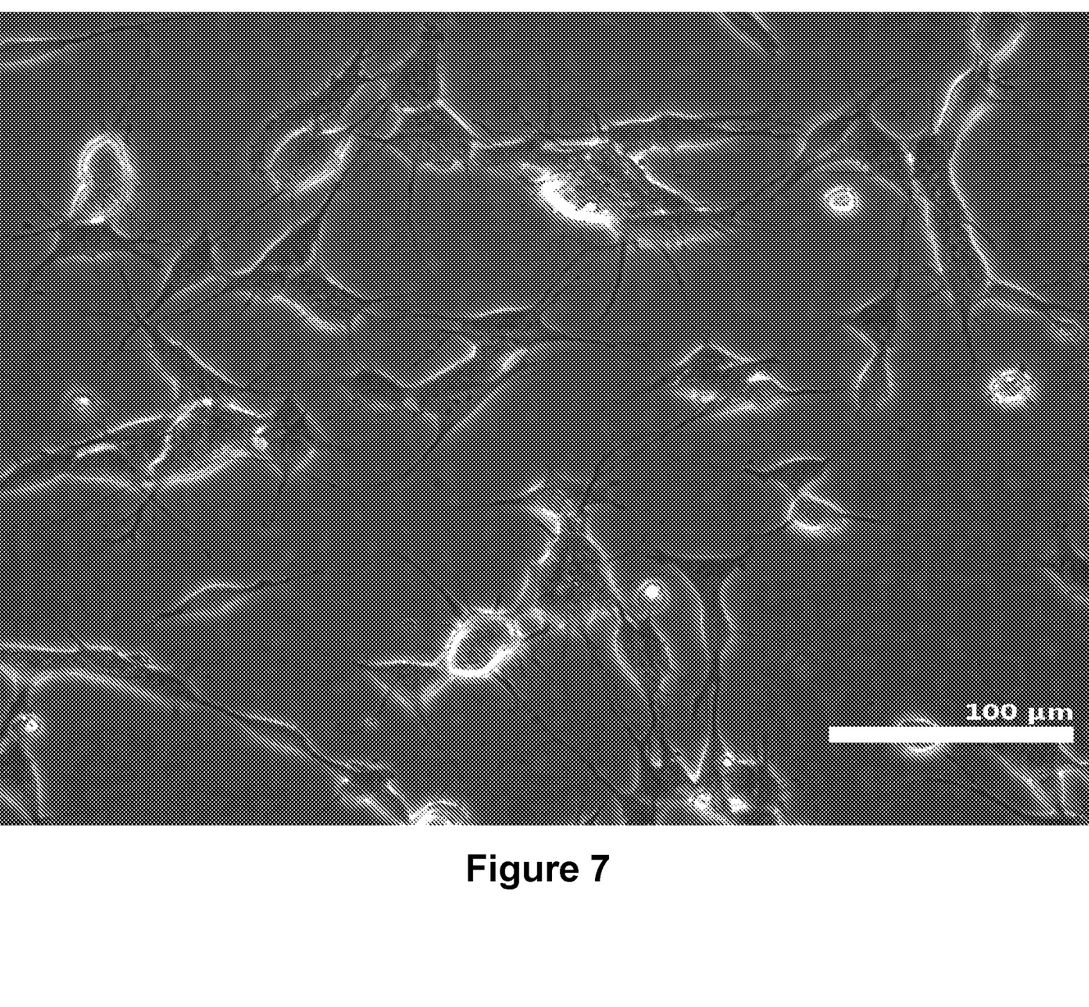
FIG. 7 is a bright field image of SH-SY5Y cells in a culture flask.

Various experiments have been conducted to test the efficacy of the sensor. FIG. 7 is a bright field image of SH-SY5Y cells in a culture. Displacement calculations were performed for two different positions of the sensor where cells were growing well separated from each other. Evaluating forces from individual cells in areas with many cells very close or even growing on top of each other would be more difficult because of an overlap between displacements produced by the different cells.

Figure 8:
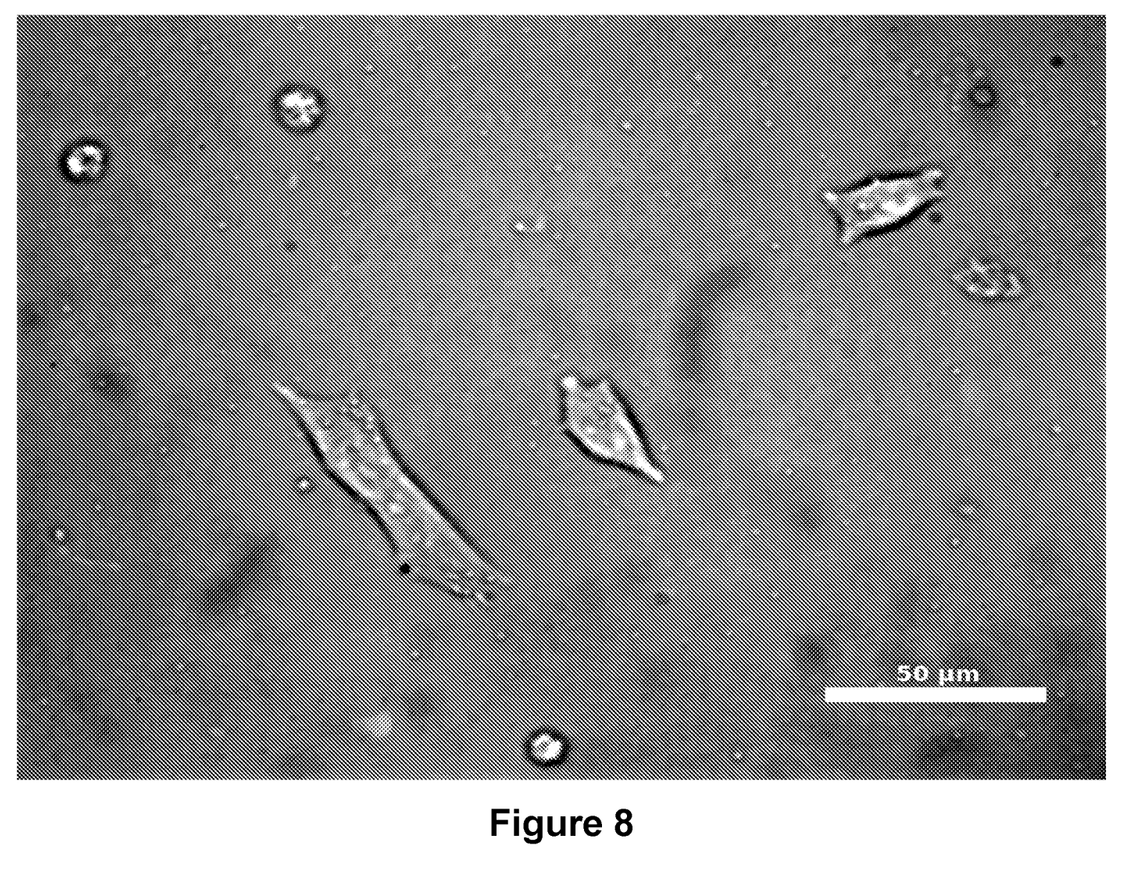
FIG. 8 is a bright field image of three of the cells of the image of FIG. 7 on a cell force sensor of FIGS. 2 and 3.
Figure 9:
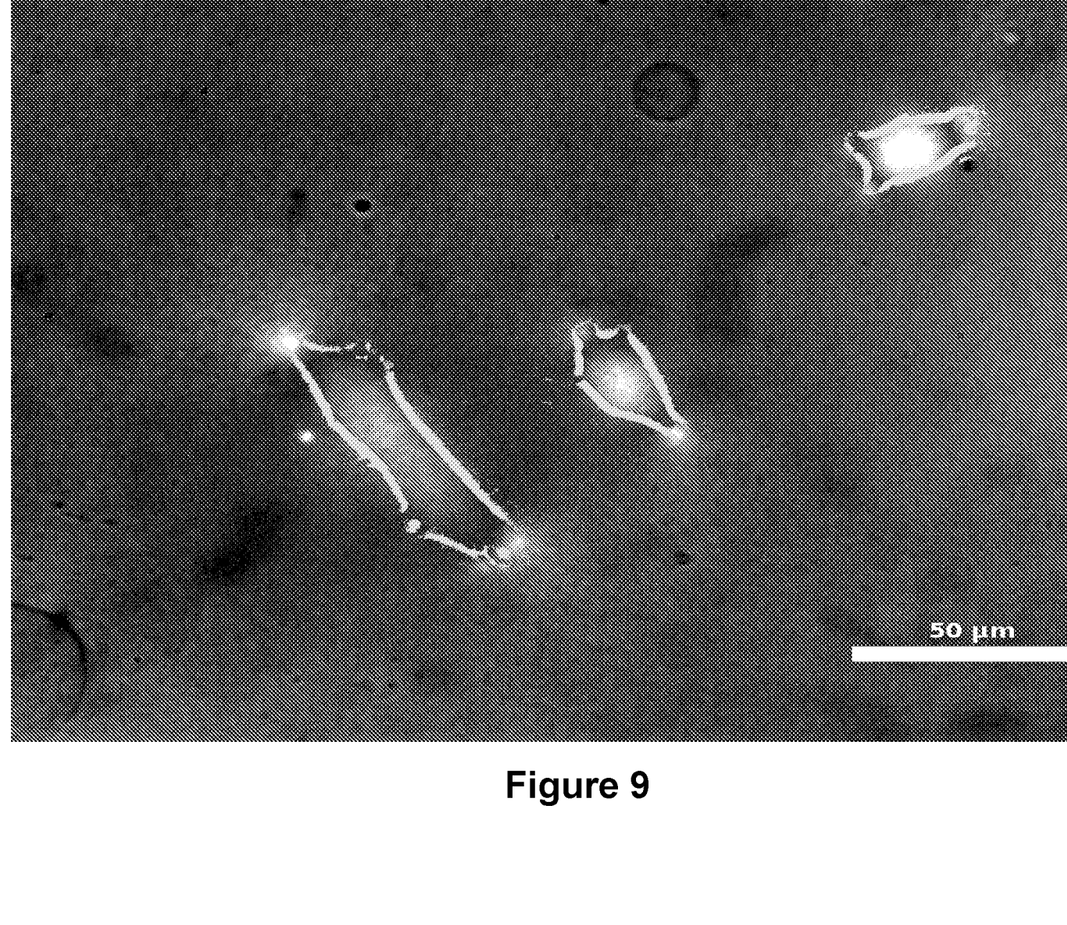
FIG. 9 is an interference image at 599 nm of the cells, in which the contrast is enhanced and green contours represent the edges of the cells.

FIG. 8 is a bright field image of three of the cells shown in FIG. 7, cultured on a force sensor. After acquiring the bright field image, a scan from 550 nm-750 nm was performed without changing the position of the sensor. The image taken at λ=599 nm, shown in FIG. 9, shows bright and dark regions which correspond to the cell position (contours). After this measurement, the total thickness at every pixel was calculated.

Figure 10:
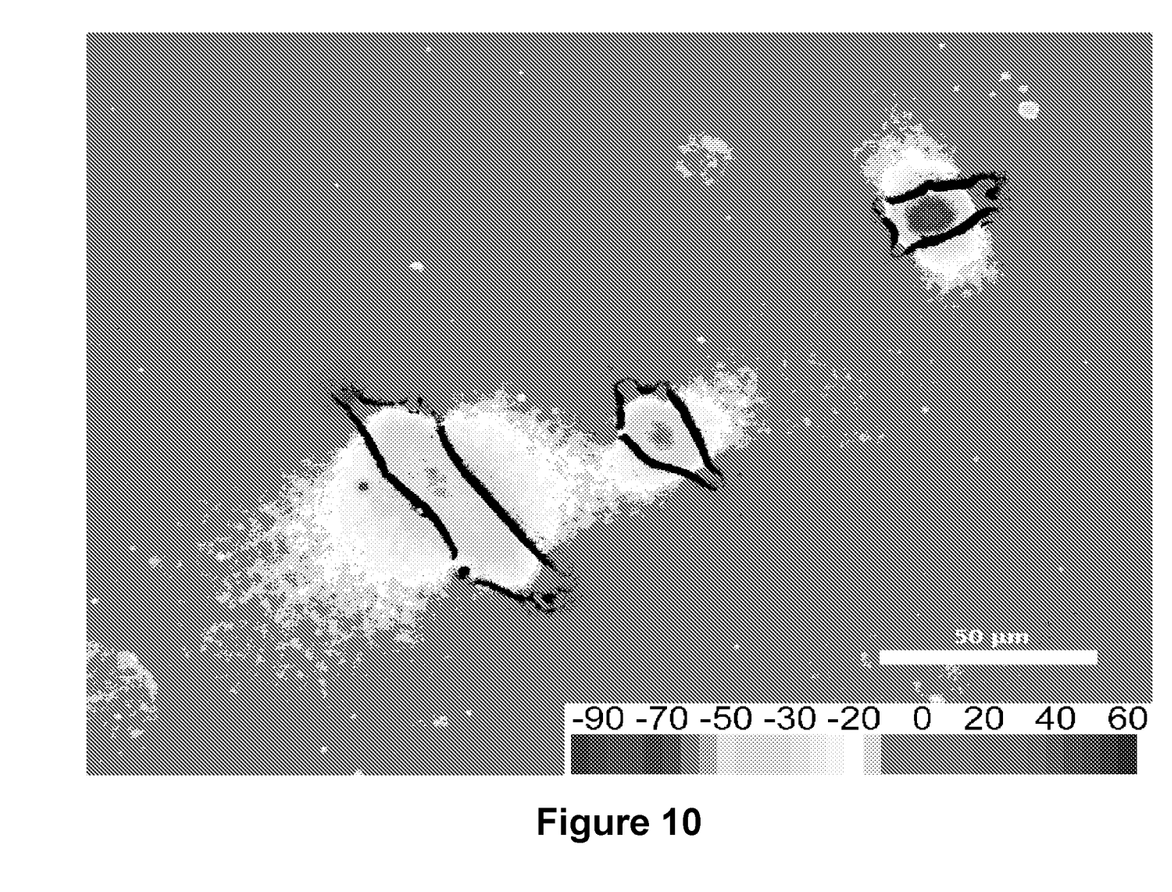
FIG. 10 is a relative thickness map of displacements produced by SH-SY5Y cells; here the colour scales correspond to displacements in nanometres and the black contours represent the edges of the cells.

Since the displacement and not the total thickness is the interesting quantity, a plane describing the sensor thickness in the region of interest was subtracted from the calculated total thickness map. The plane was obtained by calculating the average of 16 values at each corner of the calculated thickness map and interpolating a plane using the 4 values in the corners. The relative displacement map can be seen in FIG. 10. The black areas are the contours of the cells obtained by applying an edge detection algorithm to the bright field image. Most of the areas of the sensor where no cells are present are very flat (with +/−10 nm of the mean thickness, grey colour code). This is important for correctly detecting thickness changes without taking a reference image of the sensor without cells. Additionally, a systematic force pattern can be observed for all three cells. The cells are pulling at the edges at focal adhesions and pushing in the middle with the cell body. Areas where pulling is observed coincide with protrusions at the edges of the cells.

The sensor of the present invention can be used to measure the strength of cellular adhesion. This can be done in a number of ways. For example, a cell or a colony of cells attached to the sensor could be exposed to a (laminar) flow of medium, typically a fluid. Alternatively, the cell could be picked up using a micromanipulator. In both scenarios, recording the maximum deformation at the point just before the cell loses contact with the sensor provides a quantitative measure of the strength of adhesion at the different adhesion sites of the cell.

For the laminar flow option, the sensor of the invention could be integrated into a flow chamber such that there is a laminar or turbulent flow of fluid directly above the surface of the sensor. Cells cultured on the sensor surface are then subject to a horizontal drag force generated by this flow. The flow of liquid can be generated by connecting the flow chamber to a syringe pump or a pressure controller. The flow chamber itself can be designed and fabricated using microfluidic technology known in the art.

For the micromanipulator option, one possibility is to equip the manipulator with an ultrafine glass capillary (orifice in the micrometer range) to which a positive or negative pressure can be applied. By applying negative pressure the cell can be attached to the glass capillary, negative pressure releases the cell again. Alternatively biochemical adhesives can be used to form a more permanent but tighter contact between cell and micromanipulator. In either case, by moving the micromanipulator upwards or parallel to the surface of the sensor, the cell is pulled away from its present location leading to a deformation of the sensor surface that is proportional to the applied force.

The sensor of the present invention can be used to detect forces applied by all live cell types, i.e. eukaryotic cells, such as mammalian cells, and plants cells, and prokaryotic cells, such as bacterial cells. Also, the sensor can be used to detect the force applied by single cells or colonies of cells, such as bacteria biofilms, and fungi.

The measurement principles outlined above are the same for all cells. However, there may be some differences in how the cells are handled depending on the cell type. For example, the medium in which the cells are cultured is specific to cell type. Also the temperature of operation varies (generally 37° C. for most mammalian cells, room temperature for bacteria). Likewise oxygen concentration in the medium may vary, e.g. to study the effect of oxygen deprivation. In moving from single cells to colonies of cells, the field of view of the system can be increased by exchanging the microscope objective. Large colonies may exert a larger total force and pressure. The sensitivity of the sensor may be adjusted for this by selecting an elastic material with suitable stiffness.

A skilled person will appreciate that variations of the enclosed arrangement are possible without departing from the invention. For example, whilst in some of the examples described above, force is applied through cell focal adhesions, it will be appreciated that force could be applied by other parts of a cell, or even by cells that do not have focal adhesions, e.g. bacteria or some neuronal cells. Accordingly, the above description of the specific embodiment is made by way of example only and not for the purposes of limitations. It will be clear to the skilled person that minor modifications may be made without significant changes to the operation described.

The invention claimed is:

1. A system for measuring cellular forces exerted on a surface comprising:
   a variable wavelength light source that emits light having variable wavelengths and that performs a wavelength scan comprising emitting light over a wavelength scan range; and
   a sensor comprising:
      a first layer, wherein the first layer at least partially reflects the light emitted from the variable wavelength light source and wherein the first layer comprises a resiliently deformable surface adapted to deform on application of a cellular force;

a further layer that reflects and transmit the light emitted from the variable wavelength light source; and an elastomer layer provided between the first layer and the further layer;

wherein the first layer and the further layer define an optical cavity such that the elastomer layer is included in the optical cavity, wherein, in use, light provided to the optical cavity is at least partially reflected by the first layer and at least partially reflected by the further layer, to form an interference pattern in the optical cavity, wherein the optical cavity comprises an undeformed thickness, wherein the application of the cellular force to the resiliently deformable surface of the first layer causes a change in thickness of the optical cavity, and wherein the interference pattern formed between the first layer and the further layer is dependent on the thickness of the optical cavity and a respective wavelength of the light emitted from the variable wavelength light source such that reflectivity of light is reduced at a resonant wavelength, and wherein the variable wavelength light source is positioned relative to the sensor such that, in use, light emitted from the variable wavelength light source is first transmitted by the further layer and then reflected by the first layer;

wherein the system further comprises:

an optical detector that optically detects light emitted from the optical cavity as a function of the wavelengths of the light to detect a thickness change of the optical cavity, wherein the thickness change is dependent on the cellular force applied to the resiliently deformable surface, and wherein the optical detector identifies at least one resonant wavelength in the wavelength scan range using the detected light and determines the thickness change based on the identified at least one resonant wavelength.

2. The system as claimed in claim 1, wherein the optical detector is operable to detect light reflected from the first layer thereby to detect deformation.

3. The system as claimed in claim 1, wherein at least one of the first layer and the further layer comprises metal.

4. The system as claimed in claim 1, wherein the first layer and the further layer include gold.

5. The system as claimed in claim 1, wherein the optical detector comprises multiple pixels, wherein each pixel is associated with an area of the resiliently deformable surface and each pixel detects light so that the cellular force is determined at different areas of the resiliently deformable surface.

6. The system as claimed in claim 1, wherein the cellular force is cellular adhesion force.

7. The system as claimed in claim 1, further comprising an adhesive layer including SiO2 between the further layer and the elastomer layer.

8. The system as claimed in claim 1, wherein the resiliently deformable surface comprises a coating to provide binding sites for cell adherence.

9. The system of claim 1, wherein the optical detector identifies the at least one resonant wavelength as a wavelength in the wavelength scan range that results in minimum reflectivity.

10. A method for measuring cellular forces exerted on a surface using the system of claim 1, the method comprising:

transmitting light into the optical cavity when a cell is on the resiliently deformable surface;

detecting light emitted from the optical cavity; and using the detected light to determine the cellular force.

11. A method as claimed in claim 10, further comprising varying the wavelengths of the light transmitted into the optical cavity and detecting the light emitted from the optical cavity as the function of the wavelengths.

12. A method as claimed in claim 11, further comprising using the detected light to identify the identified at least one resonant wavelength and using the identified at least one resonant wavelength to determine the cellular force.

13. A method as claimed in claim 10, wherein the optical detector has multiple pixels, each pixel being associated with an area of the resiliently deformable surface, and wherein light is detected at each pixel so that cellular force is determined at different areas of the resiliently deformable surface.

14. A method as claimed in claim 10, wherein the cellular force measured includes cellular adhesion force.

15. A method as claimed in claim 14, further comprising removing a cell from the resiliently deformable surface, wherein the force at which the cell is removed from the resiliently deformable surface represents the cellular adhesion force.

16. A method as claimed in claim 15, wherein removing the cell includes using a fluid flow to remove the cell from the resiliently deformable surface.

17. A method as claimed in claim 15, wherein removing the cell includes using a mechanical device to pull the cell from the resiliently deformable surface.

18. A method as claimed in claim 15, wherein removing the cell includes using a suction device to pull the cell from the resiliently deformable surface.

19. A system, comprising:

a variable wavelength light source that emits light of varying wavelengths over a wavelength scan range during a wavelength scan;

a sensor including a micro-cavity that receives the wavelengths of light emitted from the variable wavelength light source, the micro-cavity comprising:

a first layer having a resiliently deformable surface that deforms on application of a cellular force, wherein the resiliently deformable surface at least partially reflects the wavelengths of light emitted from the variable wavelength light source;

a further layer that is distinct from the first layer and that reflects and transmits the wavelengths of light emitted from the variable wavelength light source, wherein the further layer is closer to a side of the micro-cavity that receives the wavelengths of light than the first layer such that the light emitted from the variable wavelength light source is first transmitted by the further layer and then reflected by the first layer; and an elastomer layer between the first layer and the further layer, wherein, during operation of the sensor, the first layer, the further layer, and the elastomer layer generate an interference pattern from light received by the micro-cavity, wherein the interference pattern is based on the cellular force and a respective wavelength of the light emitted from the variable wavelength light source and received by the micro-cavity; and an optical detector that detects, for each of the wavelengths of light emitted by the variable wavelength light source, light reflected from the micro-cavity to the optical detector, determines at least one resonant wavelength as a wavelength in the wavelength scan range that has a minimum detected reflection, detects a thickness change of the micro-cavity based on the at least one resonant wavelength, and that measures the cellular force based on the detected thickness change.

* * * * *